United States Patent [19]

Andersson et al.

[11] Patent Number: 5,780,508

[45] Date of Patent: Jul. 14, 1998

[54] PHARMACOLOGICAL PREPARATIONS COMPRISING A CYSTINE DERIVATIVE

[75] Inventors: Carl-Magnus Alexander Andersson; Håkan Sten Axel Bergstrand; Anders Rudolf Hallberg, all of Lund; Bengt Olof Särnstrand, Bjärred; Anders Per Sigvard Tunek, Malmö, all of Sweden

[73] Assignee: Astra Aktiebolag, Sodertalje, Sweden

[21] Appl. No.: 457,004

[22] Filed: Jun. 1, 1995

Related U.S. Application Data

[63] Continuation of Ser. No. 949,648, filed as PCT/SE91/00388, Jun. 3, 1991, Pat. No. 5,441,976.

[30] Foreign Application Priority Data

Jun. 8, 1990 [SE] Sweden ................................. 9002067
Jun. 28, 1990 [SE] Sweden ................................. 9002275

[51] Int. Cl.$^6$ ...................... A61K 31/195; C07C 321/04
[52] U.S. Cl. ...................... 514/562; 514/564; 514/566; 562/557
[58] Field of Search ............................ 514/562, 563, 514/564, 566; 562/557

[56] References Cited

U.S. PATENT DOCUMENTS

| 3,878,305 | 4/1975 | Damico et al. ...................... 426/104 |
| 3,952,115 | 4/1976 | Damico et al. ...................... 426/590 |
| 4,708,965 | 11/1987 | Morgan ................................. 514/563 |
| 4,724,239 | 2/1988 | Morgan ................................. 514/563 |
| 4,827,016 | 5/1989 | Morgan ................................. 560/16 |
| 5,254,579 | 10/1993 | Poli et al. ............................ 514/422 |

FOREIGN PATENT DOCUMENTS

| 0300100 | 1/1989 | European Pat. Off. |
| 008205M | 10/1970 | France |
| 2503151 | 10/1982 | France |
| 2326444 | 12/1973 | Germany |
| 2097256 | 11/1982 | United Kingdom |

OTHER PUBLICATIONS

Martin, "N-Acyl- and N-Sulfonylcysteine Derivatives," J. Med. Chem., vol. 12, pp. 950–953 (1969).

Sjodin et al., "Metabolism of N-Acetyl-L-Cysteine ....," Biochem. Pharm., vol. 38, No. 22, pp. 3981–3985 (1989).

Schaad et al., "Linear Regression Analysis of Inhibitory Potency of Organic Disulfides against Histoplasma capsulation", J. Med. Chem, vol. 18, No. 4, pp.344–351 (1975).

Kahns et al., "Prodrugs as drug delivery systems ...., " Int. J. Pharmaceutics, vol. 62, pp. 193–205 (1990).

Bowman et al., "Reactions of Thiolate Anions With 2–Substituted –2–Nitropropanes," Tetrahedron Letters, vol. 22, No. 6, pp. 1551–1554 (1981).

Kemp et al., "Templates for Intramolecular O, N–Acyl Transfer via Cyclic Intermediates ....," J. Org. Chem, vol. 54, pp. 3853–3858 (1989).

Patent Abstracts of Japan, vol. 12, No. 47 , C475, abstracts of JP 62–195356, publ. 1987–08–28, Seiwa Kasei K. K.

*Primary Examiner*—Gary Geist
*Assistant Examiner*—Rosalynd Keys
*Attorney, Agent, or Firm*—White & Case L.L.P.

[57] ABSTRACT

The invention concerns pharmaceutical preparations for stimulation of the immune system which comprise a cystine derivative as active ingredient.

2 Claims, No Drawings

PHARMACOLOGICAL PREPARATIONS COMPRISING A CYSTINE DERIVATIVE

This application is a continuation of application Ser. No. 07/949,648, filed as PCT/SE91/003, Jun. 3, 1991,U.S. Pat. No. 5,441,976.

FIELD OF THE INVENTION

The present invention relates to a new medical use of N,N'-diacetylcystine, N,N'-dibutyrylcystine, N,N'-diisovalerylcystine, N, N'-dicaprylylcystine, N,N'-diacetylcystine dimethyl ester, N,N'-diacetylcystine diethyl ester and N,N'-diisovalerylcystine dimethyl ester in racemic forms or in the form of optical D or L isomers.

In particular the invention relates to the use of the abovementioned compounds for the preparation of medicaments with immunomodulating action, particularly immunostimulating action.

BACKGROUND OF THE INVENTION

N-Acetyl-L-cysteine is a compound widely used for treating chronic obstructive airway diseases/chronic bronchitis (for further references see Multicentre Study Group. Long-term oral acetylcysteine in chronic bronchitis. A double-blind controlled study. Eur. J. Respir. Dis. 1980, 61 (suppl. 111), 93–108; Boman, G., Backer, U., Larsson, S., Melander, B., and Wahlander, L. Oral acetylcysteine reduces exacerbation rate in chronic bronchitis. Report of a trial organized by the Swedish Society for Pulmonary Disease. Eur. J. Respir. Dis. 1983, 64, 405–415; and British Thoracic Society Research Committee. Oral N-acetylcysteine and exacerbation rates in patients with chronic bronchitis and severe airway obstruction. Thorax 1985, 40, 832–835). The mechanism of action of the compound is not disclosed; its effect has been attributed to mucolytic properties (see Multicentre Study Group. Long-term oral acetylcysteine in chronic bronchitis. A double-blind controlled study. Eur. J. Respir. Dis. 1980, 61 (suppl. 111), 93–108; Boman, G., Bäcker, U., Larsson, S., Melander, B., and Wahlander, L. Oral acetylcysteine reduces exacerbation rate in chronic bronchitis. Report of a trial organized by the Swedish Society for Pulmonary Disease. Bur. J. Respir. Dis. 1983, 64, 405–415; and British Thoracic Society Research Committee. Oral N-acetylcysteine and exacerbation rates in patients with chronic bronchitis and severe airway obstruction. Thorax 1985, 40, 832–835), antioxidant properties (see Aruoma, O. I., Halliwell, B., Hoey, B. M., and Butler, J. Free Radical Biol. Med. 1989, 6, 593–597), and also immunomodulating properties (see Bergstrand, H., Bjornson, A., Eklund, A., Hernbrand, R., Eklund, A., Larsson, K., Linden M., and Nilsson, A. Stimuli-induced superoxide radical generation in vitro by human alveolar macrophages from smokers: Modulation by N-Acetylcysteine treatment in vivo. J. Free Radicals Biol. & Med. 2, 1986, 119–127).

The present invention deals with the disulfide of N-acetylcysteine, that is N,N'-diacetylcystine (in the following referred to as DiNAC), i.e. the compound of the formula:

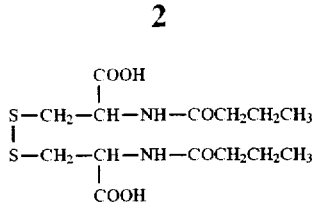

N,N'-dibutyrylcystine (in the following referred to as diBUT), i.e. the compound of the formula:

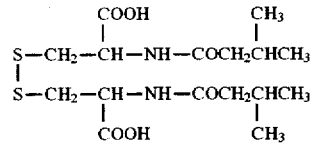

N,N'-diisovalerylcystine (in the following reffered to as diVAL), i.e. the compound of the formula

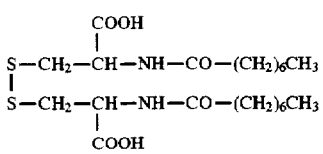

N,N'-dicaprylylcystine (in the following referred to as diCAP), i.e. the compound of the formula

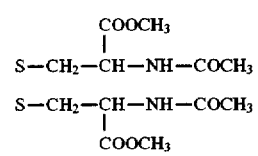

N,N'-diacetylcystine dimethyl ester (in the following referred to as diMeNAC), i.e. the compound of the formula:

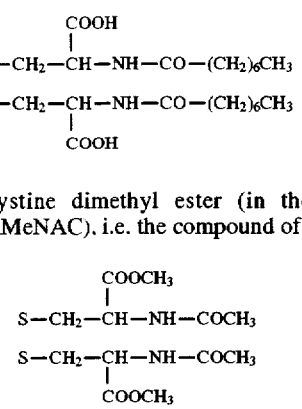

N,N'-diacetylcystine diethyl ester (in the following referred to as diEtNAC), i.e. the compound of the formula:

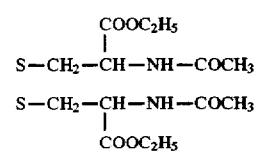

and N,N'-diisovalerylcystine dimethyl ester (in the following referred to as diMeVAL), i.e. the compound of the formula:

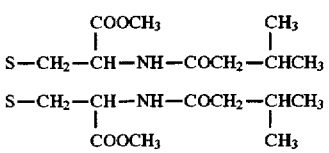

The invention also deals with the above mentioned compounds in racemic form as well as the isomeric D and L forms of the compounds. Of particular interest are the compounds having the L configuration, particularly interesting is N,N'-diacetyl-L-cystine.

The invention also deals with the compounds in the form of their physiologically acceptable salts such as the salts of sodium, potassium, ammonium, calcium or magnesium. Also included are salts of the compounds diNAC, diBUT, diVAL and diCAP with pharmaceutically acceptable organic bases.

The above mentioned compounds have previously been described in the patent literature as well as in the scientific literature. DiNAC in the following publications: U.S. Pat. No. 4,827,016; EP 300100; U.S. Pat. No. 4,724,239; U.S. Pat. No. 4,708,965; DE 2326444; Wilson, I. D., and Nicholson, J. K. Analysis of thiols and disulfides in Sulphur-containing drugs and related organic compounds. Chemistry, Biochemistry an Toxicology (ed L. A. Damani) Vol. 2A. Analytical, biochemical and toxicological aspects of sulphur xenobiochemistry. Ellis Horwood Series in Biochemical Pharmacology (Halstred Press: a division of John Wiley & Sons) Chichester 1989 p. 45; and Sjödin K., Nilsson E., Hallberg, A., and Tunek. A. Metabolism of N-Acetyl-L-cysteine. Some structural requirements for the deacetylation and consequences for the oral bioavailability. Biochem. Pharmacol. 1989, 38, 3981–3985). In U.S. Pat. No. 4,827,016 the compound is claimed to be effective for topical treatment of dermal inflammations which are induced and propagated by leuikotrienes.

The remaining compounds have also been described in the literature. (See for instance, for diMeNAC: Bowman, W. R. Richardson, G. D. Tetrahedron Lett. 1981, 22, 1551–1554; for diEtNAC: Damico, R. A. Boggs, R. W. U.S. Pat. No. 3,952,115 (1976); for diVAL, diMeVAL: Martin, T. A. J. Med. Chem 1969, 12, 950–953), for diCAP: FR. 8205 M. for diBUT: FR 2503151).

Nothing is reported or generally known concerning the pharmacological and/or therapeutic properties of these compounds with respect to immunological systems or inflammatory diseases of the lung such as chronic bronchitis.

DISCLOSURE OF THE INVENTION

It has unexpectedly been found that the hereinbefore mentioned compounds diNAC, diBUT, diVAL, diCAP, diMeNAC, diEtNAC and diMeVAL in an experimental animal model for assessing a T-cell reactivity in vivo, i.e. the delayed type hypersensitivity (DTH) reaction in the mouse ear, are highly potent and efficient immunostimulating agents, some being in the order of 100–1000 times more effective than the thiol NAC. Thus, in this model the compounds are highly effective immunostimulators with a potency and efficacy superior or equal to known immunostimulants such as diethyl dithiocarbamate (DTC) or hydroxyethyl disulfide (HEDS; see St Georgiev, V. New synthetic immunomodulating agents. Trends in Pharmacological Science 1988, 446–451).

Therefore, the compounds DiNAC, diBUT, diVAL, diCAP, diMeNAC, diEtNAC, diMeVAL and their D and L optical isomers may be used for treatment of diseases where a defect in the immune system and/or an ineffective host defence is at hand or can be suspected.

Examples of such diseases are chronic bronchitis and other inflammatory diseases of the airways such as asthma and rhinitis but also certain forms of autoimmune diseases like diabetes and rheumatoid arthritis and/or various malignant diseases. HIV infection or AIDS may be treated with the compounds. Also atherosclerotic disease may be treated with the compounds.

Effective amounts of the compounds diNAC, diBUT, diVAL, diCAP, diMeNAC, diEtNAC, diMeVAL and their D and L optical isomers for use in the treatment of the above mentioned diseases are in the range 0.5–500 mg, preferably 5–50 mg, daily dose.

Synthesis of compounds

The compounds diNAC, diBUT, diVAL and diCAP may be prepared, for example, from L-cystine via acylation (see U.S. Pat. No. 4,827,016; EP 300100; U.S. Pat. No. 4,724, 239; U.S. Pat. No. 4,708,965; DE 2326444; Marshall, R., Winitz, M., Birnbaum, S. M. and Greenstein, J. P. J. Am. Chem. Soc. 1957, 79, 4538–4544; and Cecil, R. McPhee, J. B. Biochem. J. 1957, 66, 538–543) or through oxidative dimerization of the appropriate acylcysteines (see Snow, J. T., Finley, J. W. Friedman, M. Biochem. Biophys. Res. Commun. 1975, 64, 441–447).

The esters diMeNAC, diEtNAC and diMeVAL may be synthesized analogously, i.e. by acylation of the cystine methyl or ethyl esters as appropriate or by oxidative dimerisation of the respective N-acetyl cystine methyl or ethyl esters or N-isovalerylcysteine methyl ester. For examples of preparations, see Bonnett, R., Nicolaidow, P. J. Chem. Soc. Perkin Trans. I 1979, 1069–1077. Schaad, L. J., Werner, R. M., Dillon, L., Field, L., Tate, C. E. J. Med. Chem. 1975, 18, 344–351, and Martin, T. A. J. Med. Chem. 1969, 12, 950–953.

Effects of compounds in a model of delayed type hypersensitivity in the mouse

The property of the compounds diNAC, diBUT, diVAL, diCAP, diMeNAC, diEtNAC and diMeVAL to stimulate immune responses is illustrated by their efficacy in a model of the delayed type hypersensitivity (DTH) reaction in the mouse.

Both male and female Balb/c mice obtained from Bomholtsgaard (Denmark) and Charlie Rivers (England), were used at the weight of 18–20 gram. 4-ethoxymethylene-2-phenyloxazolone (OXA) was purchased from BDH (England) and served as an antigen in this test.

The mice were sensitized, Day 0, by epicutaneous application of 150 μl absolute ethanol-acetone (3:1) solution containing 3% OXA on the shaved thorax and abdomen. Treatment with the L-form of diNAC, diMeNAC, diEtNAC, diMeVAL, or vehicle (phosphate buffer, pH 7.0) was initiated by oral feeding immediately after sensitization and continued once daily to Day 6. Seven days (Day 6) after the sensitization both ears of all mice were challenged on both sides by topical application of 20 μl 1% OXA dissolved in peanut oil. Ear thickness was measured prior to and 24 or 48 hours after challenge using an Oditest spring calliper. Challenges and measurements were performed under light pentobarbital anesthesia. The intensity of the DTH reactions was expressed according to the formula: $T_{t24/48}-T_{t0}$ μm units, where t0, t24 and t48 represent the ear thickness before and 24 or 48 hours after challenge, respectively, in an individual test (T). The results were expressed as the mean +/-S.E.M. The level of significance between means of the groups was obtained by Student's two-tailed t-test. Tables 1 and 2 show the results from 24 and 48 hours measurements, respectively, from a representative experiment with the L-form of diNAC. The results show that L-diNAC, after oral administration, caused a significant increase of the ear thickness in a concentration-response manner.

TABLE 1

Ear thickness 24 hours after challenge of animals treated with the indicated doses of L-diNAC or vehicle.

| Conc. μmol/kg | N | Diff. $T_{t24}-T_{t0}$ | S.E.M. | Sign. |
|---|---|---|---|---|
| Buffer | 13 | 7.85 | 0.32 | |
| NaCl | 10 | 7.90 | 0.30 | n.s. |
| 0.03 | 10 | 13.75 | 0.47 | *** |
| 0.30 | 10 | 15.70 | 0.48 | *** |
| 3.0 | 10 | 18.30 | 1.02 | *** |
| 30.0 | 15 | 20.67 | 0.67 | *** |

***: p < 0.001

TABLE 2

Ear thickness 48 hours after challenge of animals treated with the indicated doses of L-diNAC or vehicle.

| Conc. µmol/kg | N | Diff. $T_{t48} - T_{t0}$ | S.E.M. | Sign. |
|---|---|---|---|---|
| Buffer | 14 | 9.64 | 0.35 | |
| NaCl | 10 | 9.85 | 0.54 | n.s. |
| 0.03 | 10 | 11.65 | 0.27 | *** |
| 0.30 | 10 | 12.65 | 0.48 | *** |
| 3.0 | 10 | 14.95 | 0.55 | *** |
| 30.0 | 15 | 13.63 | 0.30 | *** |

***: $p < 0.001$

Table 3 gives the correponding figures for ear thickness 24 and 48 hours after challenge of animals treated with diMeNAC and diEtNAC.

TABLE 3

Ear thickness 24 and 48 hours after challenge of animals treated with the L-forms of diMeNAC and diEtNAC.

| | Conc µmol/kg | N | Diff $T_{t24} - T_{t0}$ | S.E.M. | Sign. |
|---|---|---|---|---|---|
| 24 h | | | | | |
| Buffer | | 10 | 8.70 | 0.34 | — |
| diMeNAC | 0.03 | 10 | 18.00 | 0.84 | *** |
| | 3.0 | 10 | 12.55 | 0.88 | ** |
| diEtNAC | 0.03 | 10 | 11.75 | 0.62 | *** |
| | 3.0 | 10 | 13.05 | 0.59 | *** |
| 48 h | | | | | |
| diMeNAC | 0.03 | 10 | 12.85 | 0.67 | ** |
| | 3.0 | 10 | 13.35 | 0.67 | *** |
| diEtNAC | 0.03 | 10 | 13.15 | 0.53 | *** |
| | 3.0 | 10 | 13.20 | 0.66 | *** |

**: $p < 0.01$
***: $p < 0.001$

Pharmaceutical formulations

The described active substances can be included in different dosage forms e.g. tablets, coated tablets, gelatin capsules, solutions and aerosols.

For the preparation of tablets, coated tablets and gelatin capsules the active substances can be combined with pharmaceutically acceptable materials, e.g. lactose, starch, dicalcium phosphate, microcrystalline cellulose, polyvinylpyrrolidone, gelatin, cellulose derivatives, colloidal silicone dioxide, talc and stearic acid or its salts.

For the preparation of oral solutions suitable excipients are water, saccharose, glucose, sorbitol, fructose and xylitol.

The dosage forms can besides mentioned excipients contain preservatives, stabilizers, viscosity regulating agents, emulsifiers, sweetening agents, colouring agents, flavouring agents, tonicity regulating agents, buffers or antioxidants. They can also contain other therapeutically valuable substances.

EXAMPLE 1

Tablet containing 10 mg of active substance per tablet:
Active substance 10 mg
Lactose 100 mg
Potato starch 50 mg
Polyvinylpyrrolidone 5 mg
Microcrystalline cellulose 15 mg
Magnesium stearate 1 mg

EXAMPLE 2

Direct compression tablet containing 5 mg of active substance per tablet:

Active substance 5 mg
Lactose, anhydrous 150 mg
Microcrystalline cellulose 50 mg
Colloidal silicon dioxide 1 mg
Magnesium stearate 2 mg If desired, the obtained tablets can be film coated with e.g. hydroxypropyl methylcellulose, hydroxypropyl cellulose or dimethylaminoethyl methacrylate methacrylic acid ester copolymer.

EXAMPLE 3

Solution for injection containing active substance 1 mg/ml

Active substance 1.0 mg
Sodium chloride 8.8 mg
Water for injection to 1 ml

EXAMPLE 4

Oral solution containing active substance 1 mg/ml

Active substance 1.0 mg
Sorbitol 150 mg
Glycerin 100 mg
Disodium edetate 0.5 mg
Preservative q.s.
Flavour q.s.
Water, purified to 1 ml

EXAMPLE 5

Powder aerosol giving 1 mg per dose

The micronized active substance can be filled into a powder inhaler device e.g. Turbuhaler$^R$ giving 1 mg/dose.

We claim:

1. A peroral or parenteral pharmaceutical preparation for the treatment of diseases wherein an immunostimulating substance is effective, consisting essentially of N,N'-diacetyl-L-cystine or a physiologically acceptable salt thereof as active ingredient and a pharmaceutically acceptable carrier.

2. The pharmaceutical preparation according to claim 1 wherein the preparation comprises a form selected from the group consisting of a tablet, a coated tablet, a capsule, a powder aerosol and an injection solution.

* * * * *